United States Patent [19]

Watson et al.

[11] Patent Number: 5,736,578
[45] Date of Patent: Apr. 7, 1998

[54] ETHYLAMIDO FLUORENES AND IMPROVED METHOD OF MAKING SAME

[75] Inventors: Brett T. Watson, Verloese, Denmark; Katherine S. Takaki, Middletown, Conn.; Joseph P. Yevich, Southington, Conn.; James R. Epperson, Cromwell, Conn.; George N. Karageorge, Meriden, Conn.; Karen L. Leboulluec, Durham, Conn.

[73] Assignee: Bristol-Myers Squibb Company, Princteon, N.J.

[21] Appl. No.: 644,510

[22] Filed: May 10, 1996

Related U.S. Application Data

[63] Continuation-in-part of Ser. No. 486,153, Jun. 6, 1995, abandoned.

[51] Int. Cl.⁶ .......................... A61K 31/16; C07C 233/05
[52] U.S. Cl. .................. 514/630; 514/624; 514/625; 514/626; 514/627; 514/628; 514/629; 564/189; 564/190; 564/192; 564/193; 564/194; 564/196; 564/201; 564/204; 564/209; 564/210; 564/211; 564/212; 564/213
[58] Field of Search ...................... 564/189, 190, 564/192, 193, 194, 196, 201, 204, 209, 210, 211, 212, 213; 514/624, 625, 626, 627, 628, 629, 630

[56] References Cited

U.S. PATENT DOCUMENTS

| | | | |
|---|---|---|---|
| 4,282,170 | 8/1981 | Lavagnino et al. | 564/164 |
| 4,508,735 | 4/1985 | Lacefield et al. | 514/616 |
| 5,206,377 | 4/1993 | McAfee | 548/253 |

FOREIGN PATENT DOCUMENTS

| | | |
|---|---|---|
| 0215297 | 3/1987 | European Pat. Off. |
| 9407487 | 4/1994 | WIPO |

OTHER PUBLICATIONS

Arendt et al, Br. Med J., 292, 1170, 1986.
Assithianakis et al, Arch. Pharm., 320: 604–608, 1987.
Cassone et al, J. Biol. Rhythms, 1: 219–229, 1986.
Ebisawa et al, Proc. Natl. Acad. Sci., 91:6133–6137, 1994.
Severin et al, Chem. Ber., 110:491–498, 1977.
Stamm et al, Cem. Ber., 111:2665–2666, 1978.

*Primary Examiner*—Shailendra Kumar
*Attorney, Agent, or Firm*—David M. Morse

[57] ABSTRACT

Novel substituted fluorene compunds of Formula I are active as melatonergic agents:

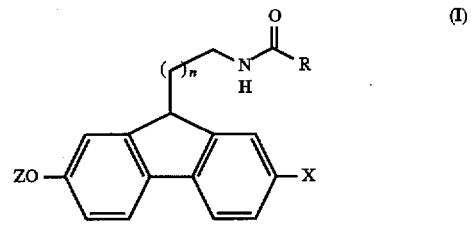

wherein:
X=H, halogen, OH or OZ;
Z=$C_{1-6}$ alkyl; —$(CH_2)_m$—$CF_3$(m=0–2); $CD_3$; or

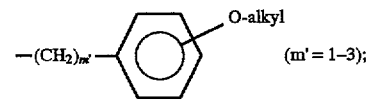

n=1 or 2; and
R=$C_{1-6}$ alkyl, $C_{3-6}$ cycloalkyl, $C_{2-4}$ alkenyl, halogen substituted $C_{1-6}$ alkyl, or $C_{1-6}$ alkoxy substituted $C_{1-6}$ alkyl.

20 Claims, No Drawings

ETHYLAMIDO FLUORENES AND IMPROVED METHOD OF MAKING SAME

This application is a continuation-in-part of U.S. Ser. No. 08/486,153 filed on Jun. 6, 1995, now abandoned.

BACKGROUND OF THE INVENTION

This application discloses novel fluorene compounds having amidoethyl substituents at the $C_9$ position. It also concerns the preparation of these compounds, as well as methods and compositions which use them. The compounds have melatonergic properties that are believed to make them useful in treating sleep disorders, e.g., jet-lag and the like.

Melatonin (N-acetyl-5-methoxytryptamine) is a hormone synthesized and secreted primarily by the pineal gland. Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

Recent evidence demonstrates that melatonin exerts its biological effects through specific receptors. Use of the biologically active, radiolabelled agonist $[^{125}I]$-2-iodomelatonin has led to the identification of high affinity melatonin receptors in the central nervous systems of a variety of species. The sequence of one such high affinity melatonin receptor, cloned from frog dermal melanophores, has been reported (Ebisawa, et al., *Proc. Natl. Acad. Sci.* 91: 6133–6137, 1994). In mammalian brain, autoradiographic studies have localized the distribution of melatonin receptors to a few specific structures. Although there are significant differences in melatonin receptor distribution even between closely related species, in general, the highest binding site density occurs in discrete nuclei of the hypothalamus. In humans, specific $[^{125}I]$-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms*, 1: 219–229, 1986). In humans, administration of melatonin has been used to treat jet-lag related sleep disturbances, considered to be caused by desynchronization of circadian rhythms (Arendt, et al., *Br. Med. J.* 292: 1170, 1986). Further, the use of a single dose of melatonin to induce sleep in humans has been claimed by Wurtman in International Patent Application WO 94/07487.

Melatonin binding sites have been found in several diverse tissues of the body—i.e., in the retina, superchiasmatic nucleus, spleen, etc. Thus, melatonin exerts multiple physiological effects, is not highly selective, and has a significant potential for producing side effects. Melatonin agonists should be more selective than melatonin and give fewer side effects.

In addition, melatonin's metabolic profile can be problematic in that the compound degrades rapidly in vivo and its oral bioavailability is often low and variable. Suitable melatonin agonists could overcome these drawbacks, resulting in products having more predictable activity.

Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, jet-lag, work-shift syndrome, sleep disorders, glaucoma, reproduction, cancer, immune disorders, and neuroendocrine disorders.

U.S. Pat. No. 5,206,377 to McAfee discloses compounds having melatonin antagonist activity which conform to formula 1:

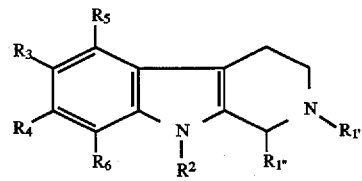

wherein $R_{1'}$ is $C_{1-6}$ alkanoyl; $R_{1''}$ is hydrogen, $C_{1-6}$ alkyl or optimally substituted phenyl; $R_2$ is hydrogen or phenyl substituted $C_{1-6}$ alkylene; and $R_3$, $R_4$, $R_5$ and $R_6$ are $C_{1-6}$ alkyl, $C_{1-6}$ alkoxy or optionally substituted phenoxy. The McAfee compounds do not contain N-amidoethyl substituents.

Stamm, et al., at *Chem. Ber.*, 111: pp. 2665–6 (1978), show the amidoethylation of fluorene with N-acylaziridines to yield compounds of formula 2:

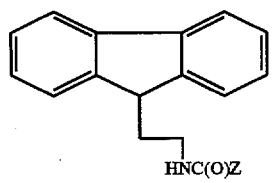

wherein Z is ethoxy, diphenylamine, diethylamine or phenyl.

Assithianakis et al., disclose compounds of formula 3 in *Arch. Pharm.*, Vol. 320, (1987), pp. 604–8:

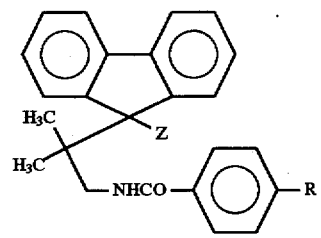

Z=H or OH; and R=H or Br.

Hansen et al. disclose, in EPO Patent publication 0215297A2, compounds of formula 4:

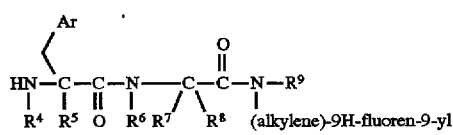

wherein Ar is an optionally substituted phenyl group, and $R^4$ through $R^9$ are H or lower alkyl. These dipeptides are used as analgesics.

Severin et al., show in *Chem, Ber.*, Vol. 110, (1977), p. 491–8, the preparation of the fluorenyl ethyl amine of formula 5:

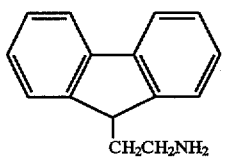

None of these publications discloses the compounds of this invention.

Summary and Detailed Description of the Invention

SUMMARY OF THE INVENTION

The invention is concerned with substituted fluorenyl compounds of formula I and compositions and methods which employ them.

Formula I is:

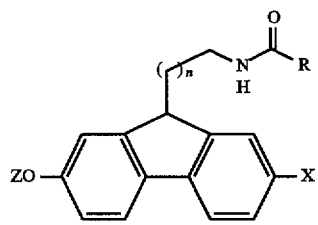

wherein:

X=H, halogen, OH or OZ;

Z=$C_{1-6}$ alkyl; —$(CH_2)_m$—$CF_3$ (m=0–2); $CD_3$; or

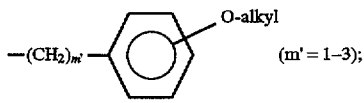

n=1 or 2; and

R=$C_{1-6}$ alkyl, $C_{3-6}$ cycloalkyl, $C_{2-4}$ alkenyl, halogen substituted $C_{1-6}$ alkyl, or $C_{1-6}$ alkoxy substituted $C_{1-6}$ alkyl.

The melatonergic agents of the invention have several advantages over similar agents. They perform well in tests which demonstrate affinity for the melatonin binding site found in human suprachiasmatic nucleus (SCN). Many of the compounds have $IC_{50}$ values for melatonin binding of 250 nM or less.

The instant compounds are agonists as determined by their melatonin-like ability to block the forskolin-stimulated accumulation of cyclic AMP in certain cells. Also, many of these compounds are able to affect activity rhythms in rodents, indicating the ability to moderate circadian rhythms in mammals.

These and other advantages will become more apparent after consideration of the specification and claims.

DETAILED DESCRIPTION

The new melatonergic agents described herein conform to formula I:

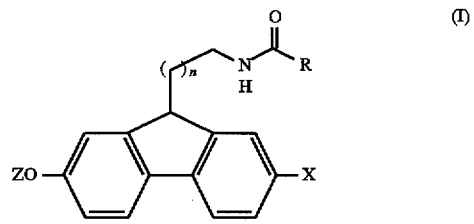

wherein:

X=H, halogen, OH or OZ;

Z=$C_{1-6}$ alkyl; —$(CH_2)_m$—$CF_3$ (m=0–2); $CD_3$; or

n=1 or 2; and

R=$C_{1-6}$ alkyl, $C_{3-6}$ cycloalkyl, $C_{2-4}$ alkenyl, halogen substituted $C_{1-6}$ alkyl, or $C_{1-6}$ alkoxy substituted $C_{1-6}$ alkyl.

By "alkoxy", applicants mean alkoxy groups, —O-alkyl, having branched or straight chains. Methoxy groups are among the preferred alkoxy groups.

By "alkyl" is meant branched or straight chain $C_{n'}H_{(2n'+1)}$ group moieties and cyclic $C_{n'}H_{(2n'-1)}$ moieties. n' is the number of C atoms in these moieties. All alkyl groups in R or Z, except for cyclic ones, contain from 1 to 6 carbon atoms. Preferred alkyl groups include methyl, ethyl, isopropyl, n-propyl, cyclopropyl, and cyclobutyl.

"Alkenyl" denotes monovalent straight or branched chain moieties containing one site of unsaturation and at least 2 carbon atoms. These moieties conform to the formula $C_{n''}H_{(2n''-1)}$, with n" being the number of carbon atoms present. Preferred alkenyl moieties include vinyl.

Alkoxy substituted phenyl groups in compounds of the invention will contain from 7 to 10 carbon atoms. They may be linked to a ring of the fluorene moiety via 1 to 3 methylene (—$CH_2$—) groups. (Methoxy phenyl)propyl substituents are preferred.

Alkoxy substituted alkyl groups found in compounds of the invention contain a total of 2 to 8 carbon atoms. Any of the alkyl groups may be straight, branched or cyclic, as set out above. Preferred groups of this type include methoxymethyl.

The term "halogen" refers to Cl, Br, F or I atoms. Generally, there will be from 1 to 3 halogen substituents present in each halogen substituted alkyl moiety. Preferred halogen substituents include Cl and F. Halomethyl groups, e.g., chloromethyl and trifluoromethyl groups are preferred.

"D" refers to deuterium m can be 0, 1 or 2 and designates the number of $CH_2$ groups. m is preferably 1.

m' refers to 1, 2 or 3 and is preferably 3.

n is 1 or 2, preferably 1.

One preferred group of formula I compounds includes those wherein Z is a methyl group and X is hydrogen or a methoxy group. Among these, those in which R is methyl, n-propyl, methoxymethyl, i-propyl and vinyl are preferred. Some compounds in this group are:

N-[2-(2-methoxyfluoren-9-yl)ethyl]butanamide;

N-[2-(2-methoxyfluoren-9-yl)ethyl]acetamide;
N-[2-(2-methoxyfluoren-9-yl)ethyl]-2-propenamide;
N-[2-(2,7-dimethoxyfluoren-9-yl)ethyl]methoxyacetamide; and
N-[2-(2,7-dimethoxyfluoren-9-yl)ethyl]-2-methyl propanamide.

A second preferred group of compounds of formula I are compounds in which Z is a methyl group and X is a methoxy group. Included in this group are:
N-[3-(2,7-dimethoxyfluoren-9-yl)-prop-1-yl]propanamide;
N-[3-(2,7-dimethoxyfluoren-9-yl)-prop-1-yl]butanamide;
N-[3-(2,7-dimethoxyfluoren-9-yl)-prop-1-yl]acetamide;
N-[3-(2,7-dimethoxyfluoren-9-yl)-prop-1-yl]cyclobutane carboxamide;
N-[3-(2,7-dimethoxyfluoren-9-yl)-prop-1-yl]cyclopropane carboxamide;
N-[2-(2,7-dimethoxyfluoren-9-yl)-ethyl]but-2-enamide; and
N-[2-(2,7-dimethoxyfluoren-9-yl)-ethyl]cyclopentane carboxamide.

Among the compounds in the second group, the following are more preferred:
N-[2-(2,7-dimethoxyfluoren-9-yl)ethyl]butanamide;
N-[2-(2,7-dimethoxyfluoren-9-yl)ethyl]propanamide;
N-[2-(2,7-dimethoxyfluoren-9-yl)ethyl]cyclopropane carboxamide;
N-[2-(2,7-dimethoxyfluoren-9-yl)ethyl]acetamide;
N-[2-(2,7-dimethoxyfluoren-9-yl)ethyl]cyclobutane carboxamide; and
N-[2-(2,7-dimethoxyfluoren-9-yl)ethyl]choroacetamide.

A third preferred group are compounds wherein Z is a methyl group, X is alkoxy or alkoxyphenylalkyl and R is alkyl.

Yet another preferred group are compounds wherein $X=OZ=OCH_2CF_3$.

Compounds of formula I also encompass all solvates, particularly hydrates, thereof.

The invention also encompasses geometric and optical isomers which arise as a consequence of structural asymmetry. Separation of individual isomers is accomplished by the application of various methods known to practitioners in the art.

The compounds of the invention are made using the following general scheme:

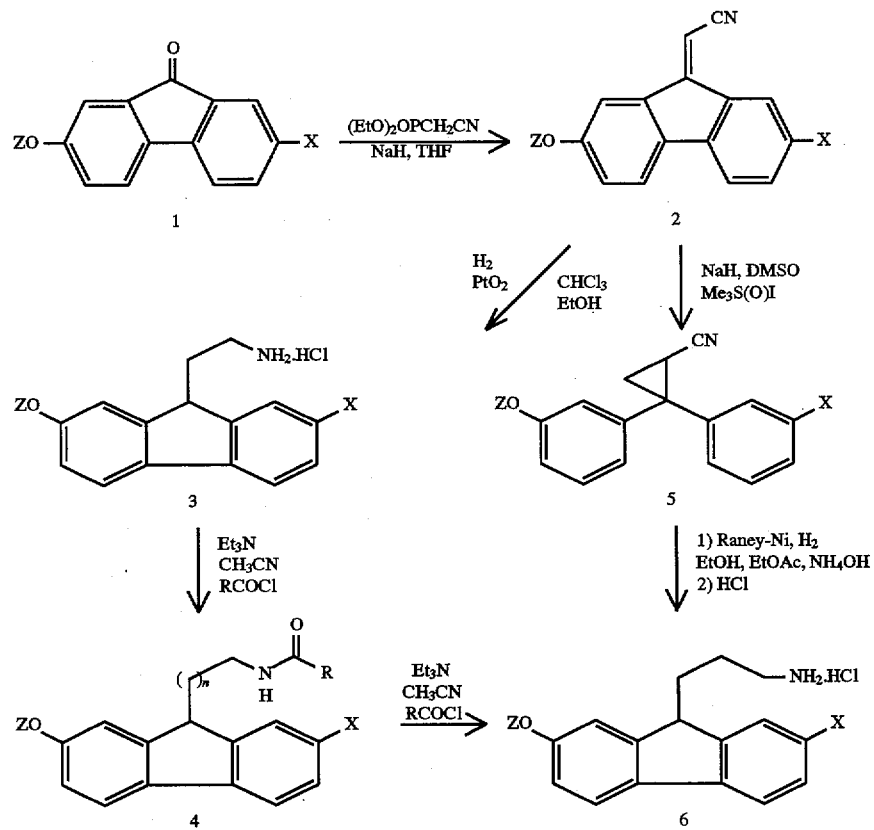

n=1 or 2
X=H, halogen or alkoxy
$Z=C_{1-6}$ alkyl; $-(CH_2)_mCF_3$; $CD_3$; or

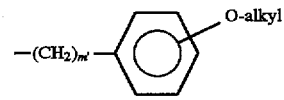

THF=tetrahydrofuran

The appropriate fluorenone is converted to the α,β-unsaturated nitrile which is then catalytically reduced to give the ethylamine hydrochloride. Alternatively, the α,β- unsaturated nitrile can be cyclopropanated and then reduced to provide the propylamine hydrochloride. Either type of amine is then converted to the desired amide using any one of a variety of acylating conditions. The use of this scheme is described in greater detail below.

The fluorenones are puchased commercially or prepared by the following general scheme:

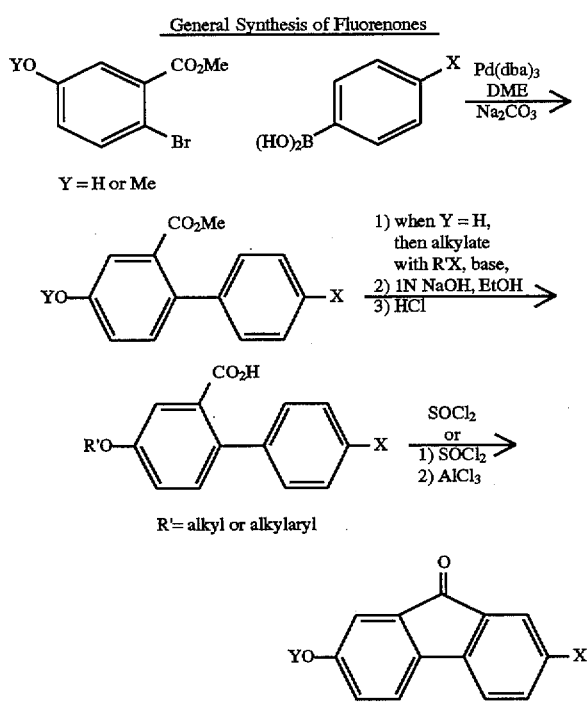

An appropriately substituted o-bromoester and phenylboronic acid are coupled using palladium catalysis to provide a biphenyl intermediate which can be alkylated on oxygen in the cases where a free phenol exists on one of the aromatic rings. The ester is then hydrolyzed to the acid which is cyclized to the desired fluorenone. The use of this scheme is described in greater detail below.

ADMINISTRATION

The compounds of the invention may be administered to patients in need of melatonergic treatment i.e., patients suffering from sleep disorders and the like, in a variety of ways. Thus, oral, transdermal, subcutaneous, intravenous, intramuscular, rectal, buccal, intranasal, and ocular routes can be used.

One or more of the compounds of the invention is mixed with pharmaceutically acceptable amounts of one or more conventional pharmaceutical excipients to produce a formulation to be administered by the desired route. Generally, such formulations will contain one or several carriers or diluents. Useful carriers include solids, semi-solids and liquids which have miscibility, or other compatibility, with the active agent(s) so that they can deliver same to a patient or host.

Suitable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate, mineral oil and the like. Mixtures are operable.

Other useful excipients include lubricants, wetting agents, gellants, emulsifiers, preservatives, colorants, perfumes, flavor enhancers, drying agents and the like. Mixtures can be employed.

Generally, compositions which include the compounds of the invention will contain from about 0.10 to about 10% of active compound(s) and 99.9 to 90%, or other suitable amounts, of excipient(s).

Dosage levels will be dictated by the patient's needs and by the medical judgment of the treating physician. Generally, however, dosages of about 0.1 mg to about 100 mg per day are useful to treat sleep or circadian rhythm disorders.

While human patients are most preferred, the compounds of the invention may be used to treat other subjects, i.e., animals preferably mammals.

SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonances (NMR) are spectral characteristics refer to Chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as a broad singlet (bs), singlet (s), multipier (m), doublet (d), or triplet (t). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using the compound neat as a film or by employing potassium bromide (KBr) as diluent. The elemental analyses are reported as percent by weight.

Unless otherwise noted, all percentages recited herein are weight percents, based on total composition weight.

The following examples describe in detail the preparation of compounds of Formula I. It will be apparent to those skilled in the art that modifications, both of materials and methods, will allow preparation of other compounds disclosed herein. From the foregoing description and the following examples it is believed that one skilled in the art is able to use the invention to the fullest extent.

The appropriate starting materials such as 2-hydroxy-9-fluorenone were purchased from commercial sources; 2,7-dihyroxy-9-fluorenone was prepared according to the methods described by Andrews et al (*Journal of Medicinal Chemistry*, 1974, 17, 882) and Agarwal (*Journal of Medicinal Chemistry*, 1967, 10, 99) or purchased from commercial sources.

EXAMPLES

These examples discuss methods of making various compounds of formula I and their biological activity.

Example 1

2-[9-(2-Methoxyfluorenyl)]ethylamine hydrochloride

A solution of 2-hydroxy-9-fluorenone (0.042 mol), potassium carbonate (0.20 mol), and methyl iodide (0.042 mol) in acetonitrile was heated to reflux overnight. The reaction mixture was cooled and the solvent removed in vacuo to yield a solid. This was dissolved in methylene chloride, washed with saturated sodium carbonate solution, dried over MgSO₄ and the solvent removed to yield a solid which was identified as 2-methoxy-9-fluorenone. To a suspension of NaH (1.61 g, 0.067 mol) in THF (200 mL) at RT was added via syringe, diethyl cyanomethylphosphonate (7.43 g, 0.042 mol); the reaction was allowed to stir for 15 min after which a pale yellow solution was observed. To this was added dropwise a solution of 2-methoxy-9-fluorenone (8.89 g, 0.042 mol) in THF (100 mL). The reaction was allowed to stir overnight at RT. The solvent was removed in vacuo and the residue was dissolved in methylene chloride, washed with water, dried over MgSO₄, and concentrated to yield an orange solid. This was dissolved in acetonitrile and washed with hexane; the acetonitrile solution was concentrated to yield an orange solid shown to be the α,β-unsaturated nitrile by $^1$H NMR. (79%) A solution/suspension of the α,β-unsaturated cyano compound (7.72 g, 0.033 mol), PtO₂ (0.77 g), CHCl₃ (23 mL), in EtOH (150 mL) was charged with H₂ (50 psi) and allowed to shake on a Parr Hydrogenation Apparatus for 18 h. The reaction mixture was then filtered and concentrated in vacuo to yield a white solid. This was washed with Et₂O and dried in vacuo to obtain a white solid (69%).

Example 2

2-[9-(2,7-Dimethoxyfluorenyl)]ethylamine hydrochloride

Prepared analogously to 2-[9-(2-Methoxyfluorenyl)] ethylamine hydrochloride in Example 1 beginning with 2,7-dihydroxy-9-fluorenone. $^1$H NMR (300 MHz, CDCl₃) δ 7.60 (d, J=8.0 Hz, 2H), 7.00 (d, J=2.0 Hz, 2H), 7.85 (dd, J=8.0, 2.0 Hz, 2H), 3.90–4.10 (m, 1H), 3.85 (s, 6H), 2.50–2.60 (m, 2H), 2.10–2.30 (m, 2H). Alternatively, the necessary intermediate 2,7-dimethoxyfluorenone was prepared as follows: Methyl 2-bromo-5-methoxybenzoate (1.60 g, 6.53 mmol), 4-methoxyphenylboronic acid (1.30 g, 8.55 mmol), and tris(dibenzylideneacetone) dipalladium (0) (0.20 g, 0.22 mmol) were added to dimethoxyethane (25 mL) and 2M sodium carbonate (25 mL). The reaction was stirred at reflux for 16 h then decanted and the residue extracted with ethyl acetate. The combined organic layers were dried (MgSO₄) and the solvent removed by rotary evaporation to afford 1.50 g of the coupled product (5.51 mmol, 84% yield). The ester (10.80 g, 39.70 mmol) was hydrolyzed with 1N sodium hydroxide (80 mL) in refluxing ethanol (500 mL). The cooled reaction mixture was extracted with methylene chloride and then acidified with 1N hydrochloric acid. The acidic solution was then extracted with methylene chloride. The organic layers were combined and the solvent was dried and concentrated by rotary evaporation to give 9.00 g (34.88 mmol, 88% yield) of the acid. 9.00 g (34.88 mmol) of the acid was dissolved in thionyl chloride (250 mL) and stirred at reflux for 6 h. The reaction was cooled to ambient temperature and the solvent was removed by rotary evaporation to give 8.20 g of 2,7-dimethoxyfluorenone (34.17 mmol, 98% yield) as a red solid.

Example 3

2-methoxy-7-pentoxyfluorenone

Methyl 2-bromo-5-hydroxybenzoate (9.30 g, 40.26 mmol), 4-methoxyphenylboronic acid (6.54 g, 43.00 mmol), and tris(dibenzylideneacetone) dipalladium (0) (0.30 g, 0.33 mmol) were added to dimethoxyethane (75 mL) and 2M sodium carbonate (75 mL). The reaction mixture was stirred at reflux for 16 h then cooled and decanted and the residue washed with ethyl acetate. The combined organic layers were dried (MgSO₄) and the solvent removed by rotary evaporation to afford 9.45 g of the coupled product (36.64 mmol, 91% yield).

The coupled product (1.06 g, 4.10 mmol) was alkylated by treating it with pentyl iodide (1.16 g, 5.85 mmol) and potassium carbonate (1.38 g, 10.00 mmol) in DMF at 75° C. for 16 h. The cooled reaction mixture was partitioned between ethyl acetate and water. The solvent was removed from the combined organic layers by rotary evaporation to give the alkylated product. The alkylated product was hydrolyzed with 1N sodium hydroxide (10 mL) in refluxing ethanol (50 mL) until the TLC indicated that the saponification was complete. The cooled reaction mixture was acidified with 1N hydrochloric acid and extracted with methylene chloride. The organic layers were dried (MgSO₄) and concentrated by rotary evaporation to give the acid. The acid was dissolved and warmed in thionyl chloride (50 mL) at 65° C. for 30 min. The solution was cooled to ambient temperature and the thionyl chloride was removed by rotary evaporation. The residue was dissolved in methylene chloride (50 mL) and aluminum chloride (0.67 g, 5.00 mmol) added. The reaction was stirred at ambient temperature for 2 h then quenched by adding the reaction mixture to a beaker containing 100 mL 1N hydrochloric acid and ice. The methylene chloride layer was separated and the acidic layer was washed with methylene chloride. The combined organic layers were dried (MgSO₄) and the solvent removed by rotary evaporation to give 1.05 g of 2-methoxy-7-pentoxyfluorenone (3.55 mmol, 87% yield) as a red solid. $^1$H NMR (300Mhz, CDCl₃) δ 7.28 (d, J=8.3 Hz, 2H), 7.14 (s, 2H), 6.93 (d, J=8.3 Hz, 2H), 3.96 (q, J=7.5 Hz, 2H), 3.82 (s, 3H), 1.80 (p, J=7.6 Hz, 2H), 1.42 (m, 4H), 0.93 (t, J=7.5 Hz, 3H).

Example 4

3-[9-(2,7-Dimethoxyfluorenyl)]propylamine hydrochloride

Sodium hydride (0.6 g, 22 mmol) was washed with hexane and suspended in 20 mL anhydrous THF under a nitrogen atmosphere. Diethyl cyanomethylphosphonate (2.8 g, 16 mmol) was added slowly in portions over 15 min. and the heterogeneous reaction mixture became a clear solution after the addition was complete. The reaction stirred for 30 min at room temperature. The ketone (4.2 g, 16 mmol) dissolved in 30 mL THF was added in portions and the reaction was refluxed overnight. The crude reaction was cooled to room temperature and then poured into 150 mL water and extracted with several portions of 40 mL CH₂Cl₂. The combined organic layers were dried over MgSO₄ and concentrated in vacuo to give a wine red solid. This α,β-unsaturated nitrile (3.9 g) was used in the subsequent reaction.

Sodium hydride (1.1 g, 44 mmol) was washed with hexane and suspended in 100 mL anhydrous DMSO under a nitrogen atmosphere. The heterogeneous reaction mixture was stirred well while portions of trimethylsulfoxonium iodide (9.9 g, 45 mmol) were added. The solution was stirred until the foaming subsided. The reaction was cooled to −60° C. and a solution of the α,β-unsaturated nitrile in 40 mL anhydrous DMSO was added in portions over 20 min. The reaction was warmed to room temperature and stirred overnight. The crude reaction was slowly poured into saturated NH₄Cl followed by the addition of EtOAc. The aqueous layer was extracted several times with EtOAc and the combined organic fractions were dried over MgSO₄ and concentrated in vacuo. The resulting light brown oil was purified by flash chromatography (EtOAc/Hexane gradient) to give the desired nitrile in 43% after 2 steps (2.1 g; mp=131°–133° C.; light yellow solid): ¹H-NMR (300 MHz, CDCl₃) δ 7.58 (m, 2H), 6.91 (m, 3H), 6.42 (m, 1H), 3.85 (s, 3H), 3.80 (s, 3H), 2.33 (m, 1H), 2.11 (m, 2H); ¹³C-NMR (75 MHz, CDCl₃) δ 158.8, 158.7, 144.9, 142.2, 120.2, 117.8, 114.1, 112.9, 106.8, 104.9, 55.5, 34.8, 21.7, 14.8; FTIR (KBr) 2833, 2237, 1623, 1582, 1470 cm⁻¹; Anal. Calc. for C₁₈H₁₅NO₂: C, 77.96; H, 5.45; N, 5.05. Found: C, 77.80; H, 5.49; N, 5.00.

The nitrile (4.3 g) was dissolved in 200 mL of a 1:1 mixture of EtOH/EtOAc and 20 mL of NH₄OH. The mixture was hydrogenated in the presence of Raney-Ni for 4hrs (TLC 1:1 EtOAc/Hex). The crude mixture was filtered, concentrated in vacuo, redissolved in CH₂Cl₂ and acetonitrile, dried over MgSO₄, filtered, and concentrated to dryness in vacuo. The resulting solid was dissolved in MeOH and acetonitrile and concentrated HCl was added (0.52 mL, 17 mmol). After concentrating to dryness, the white solid was triturated with hexane, filtered, and dried. The product was obtained in 46% (2.3 g; mp=218°–221° C.): ¹H-NMR (300 MHz, CDCl₃) δ 7.64 (d, 2H, J=8.3 Hz), 7.14 (d, 2H, J=2 Hz), 6.90 (dd, 2H, J=8.3, 2.0 Hz), 3.95 (t, 1H, J=5.2 Hz), 3.81 (s, 6H), 2.66 (t, 2H, J=8.8 Hz), 2.12–2.05 (9m, 2H), 1.30–1.20 (m, 2H); ¹³C-NMR (75 MHz, CDCl₃) δ 158.3, 147.9, 133.5, 119.8, 112.8, 110.3, 55.3, 46.3, 28.9, 22.9; FTIR (KBr) 3425, 2946, 1243 cm⁻¹; Anal. Calc. for C₁₈H₂₁NO₂●HCl●0.15 H₂O: C, 67.03; H, 6.97; N, 4.34; Found: C, 66.85; H, 7.03; N, 4.21.

Example 5

General Procedure, N-[2-(2,7-dimethoxyfluoren-9-yl)ethyl]propanamide

2-[9-(2,7-Dimethoxyfluorenyl)]ethylamine hydrochloride (0.0083 mol) was suspended in CH₃CN (150 ml) and to this was added excess Et₃N (0.024 mol). This mixture was allowed to stir until starting material was completely dissolved. Propionyl chloride (0.0083 mol) was then added and the reaction mixture was allowed to stir overnight. The acetonitrile was removed in vacuo. The residue was then washed with excess water and extracted into CH₂Cl₂. The organic layer was separated, dried (MgSO₄), filtered and concentrated in vacuo to obtain a solid which was purified by recrystallization from EtOAc/hexane. m.p. 139°–140° C.; Related compounds were purified by silica gel column chromatography or reverse phase HPLC. ¹H NMR (300 MHz, CDCl₃) δ 7.52 (d, J=8.3 Hz, 2H), 7.06 (d, J=2.4 Hz, 2H), 6.87 (dd, J=8.3, 2.3 Hz, 2H), 4.87 (bs, 1H), 3.98 (t, J=5.1 Hz, 1H), 3.83 (s, 6H), 3.04 (m, 2H), 2.29 (q, J=6.6 Hz, 2H), 1.96–1.82 (m, 2H), 0.92 (t, J=7.6 Hz, 3H); ¹³C NMR (75 MHz, CDCl₃) δ 173.4, 158.8, 147.7, 133.9, 119.9, 113.0, 110.1, 55.6, 45.7, 36.1, 31.9, 29.5, 9.49; IR (KBr) 3260, 1640, 1240 cm⁻¹; MS (DCI) m/e MH⁺=326; Analysis calc'd for C₂₀H₂₃NO₃: C, 73.82; H, 7.12; N, 4.30; found: C, 73.63; H, 7.17; N, 4.22.

Examples 6–31

The following compounds were also prepared by the general procedure outlined in Example 5 using the appropriate amine hydrochloride and acid chloride.

| Example | Compound | Melting Point (°C.) |
|---|---|---|
| 6 | N-[2-(2-methoxyfluoren-9-yl)ethyl] butanamide | 97–99 |
| 7 | N-[2-(2,7-dimethoxyfluoren-9-yl)ethyl] cyclopropane carboxamide | 152–153 |
| 8 | N-[2-(2,7-dimethoxyfluoren-9-yl)ethyl] acetamide | 147 |
| 9 | N-[2-(2,7-dimethoxyfluoren-9-yl)ethyl] methoxyacetamide | 94–95 |
| 10 | N-[2-(2,7-dimethoxyfluoren-9-yl)ethyl] butanamide | 126 |
| 11 | N-[2-(2-methoxyfluoren-9-yl)ethyl]-2-propenamide | 143–145 |
| 12 | N-[2-(2-methoxyfluoren-2-yl)ethyl] acetamide | 133–135 |
| 13 | N-[2-(2,7-dimethoxyfluoren-9-yl)ethyl] cyclobutane carboxamide | 145–146 |
| 14 | N-[2-(2,7-dimethoxyfluoren-9-yl)ethyl]-2,2-dimethyl propanamide | 88–89 |
| 15 | N-[2-(2,7-dimethoxyfluoren-9-yl)ethyl]-2-methyl propanamide | 145–146 |
| 16 | N-[2-(2,7-dimethoxyfluoren-9-yl)ethyl] choroacetamide | 122–123 |
| 17 | N-[2-(2,7-dimethoxyfluoren-9-yl)ethyl] cyclopentane carboxamide | 155–156 |
| 18 | N-[2-(2,7-dimethoxyfluoren-9-yl)ethyl] but-2-enamide | 130–132 |
| 19 | N-[3-(2,7-dimethoxyfluoren-9-yl)prop-1-yl]cyclobutane carboxamide | 110–113 |
| 20 | N-[3-(2,7-dimethoxyfluoren-9-yl)prop-1-yl]acetamide | 139–141 |
| 21 | N-[3-(2,7-dimethoxyfluoren-9-yl)prop-1-yl]butanamide | 88–90 |
| 22 | N-[3-(2,7-dimethoxyfluoren-9-yl)prop-1-yl]propanamide | 120–122 |
| 23 | N-[3-(2,7-dimethoxyfluoren-9-yl)prop-1-yl]cyclopropane carboxamide | 141–142 |
| 24 | N-[2-(2-fluoro-7-methoxyfluoren-9-yl)-ethyl]propanamide | 72–73 |
| 25 | N-[2-(2,7-di(methoxy-d₃)fluoren-9-yl)-ethyl]acetamide | 141–143 |
| 26 | N-[2-(2,7-di(methoxy-d₃)fluoren-9-yl)-ethyl]propanamide | 138–140 |
| 27 | N-[2-(2,7-di(methoxy-d₃)fluoren-9-yl)-ethyl]cyclopropane carboxamide | 133–136 |
| 28 | N-[2-(2,7-di(methoxy-d₃)fluoren-9-yl)-ethyl]butanamide | 117–120 |
| 29 | N-[2-(2-ethoxy-7-methoxyfluoren-9-yl)-ethyl]propanamide | 95–98 |
| 30 | N-[2-(2-hydroxy-7-methoxyfluoren-9-yl)-ethyl]propanamide | 50–60 |
| 31 | N-[2-(2,7-diethoxyfluoren-9-yl)-ethyl] propanamide | 225–228 |

Example 32

N-2-(2-methoxy-7-(1-pentoxy))fluorene-9-yl)ethyl propanamide.

Prepared by the general procedure outlined in example 5 using propionyl chloride. ¹H NMR (300 MHz, CDCl₃) δ 7.53 (d, J=8.3 Hz, 2H), 7.02 (s, 2H), 6.88 (d, J=8.3 Hz, 2H), 4.90 (bs, 1H), 3.95 (m, 3H), 3.84 (s, 3H), 3.04 (m, 2H), 2.30 (q, J=5.3 Hz, 2H), 1.87 (q, J=7.6 Hz, 2H), 1.77 (m, 2H) 1.43 (m, 4H), 0.93 (t, J=7.5 Hz, 6H); ¹³C NMR (75 MHz, CDCl₃) δ 173.8, 158.6, 158.2, 147.6, 134.1, 133.8, 119.8, 113.5, 113.0, 110.7, 110.1, 68.2, 55.5, 45.6, 36.0, 31.7, 29.3, 29.0, 28.1, 22.4, 13.9, 9.4. Anal. Calcd for C₂₄H₃₁NO₃●0.25 H₂O: C, 74.68; H, 8.23; N, 3.63. Found: C, 74.57; H, 8.20, N, 3.68.

Example 33

N-2-(2-methoxy-7-(3-(3-methoxyphenyl)propox-1-y))fluorene-9-yl)ethyl propanamide Prepared by the general procedure outlined in example 5 using propionyl chloride. ¹H NMR (300 MHz, CDCl₃) δ

7.54 (d, y=8.3 Hz, 2H), 7.21 (t, J=7.8 Hz, 2H), 7.03 (s, 2H), 6.91–6.73 (m, 4H), 4.92 (bs, 1H), 4.01 (m, 3H), 3.90 (s, 3H), 3.85 (s, 3H), 3.06 (q, J=6.2 Hz, 2H), 2.82 (t, J=7.9 Hz, 2H), 2.28 (q, J=6.6 Hz, 2H), 2.12 (p, J=7.8 Hz, 2H) 1.89 (q, J=7.6 Hz, 2H), 0.95 (t, J=7.6 Hz, 3H); $^{13}$C NMR (75 MHz, CDCl$_3$) δ 173.4, 158.8, 158.1, 147.7, 143.2, 133.9, 130.4, 128.4, 120.9, 118.8, 114.7, 114.2, 112.5, 112.0, 111.2, 110.2, 109.9, 109.2, 67.3, 56.5, 54.2, 46.5, 36.1, 32.2, 31.9, 30.8, 29.4, 10.4, 8.7. Anal. Calcd for $C_{29}H_{33}NO_4 \cdot 0.67\ H_2O$: C, 73.85; H, 7.34; N, 2.97. Found: C, 73.81; H, 7.02, N, 2.84.

Example 34

Measurement of Melatonergic Binding

1. Reagents
   (a) 50 mM Tris buffer containing 12.5 mM MgCl$_2$ and 2 mM EDTA (pH 7.4 at 37° C.).
   (b) Wash buffer: 20 mM Tris base containing 2 mM MgCl$_2$ (pH 7.4 at room temperature).
   (c) Melatonin ($10^{-5}$M final concn.).
   (d) 2-[$^{125}$I]-iodomelatonin (100 pM final concn.). Source: NEN
2. Membrane preparation. The receptor cDNA (human ML$_{1A}$) was subcloned into pcDNA3 and introduced into NIH 3T3 cells using Lipofectamine. Transformed NIH 3T3 cells resistant to geneticin were isolated and single colonies expressing high levels of 2-[$^{125}$I]-iodomelatonin binding were isolated and characterized. Cell pellets were frozen at −80° C. for further use. For preparing membrane homogenates, pellets are thawed on ice, and resuspended in TME buffer, Tris base, MgCl$_2$, EDTA (pH 7.4 at 37° C.), supplemented with aprotinin, leupeptin, and phenylmethlysulfonylfluoride. The cells were then homogenized using a dounce homogenizer, and centrifuged. The resulting pellet was resuspended with a dounce homogenizer in TME and frozen. On the day of assay, the small aliquot was thawed on ice and resuspended in TME buffer.
3. Incubation: 37° C. for 1 hour. Reaction is terminated by filtration.

The procedure was based on that disclosed in: Reppert, S. M., Weaver, D. R., and Ebisawa, R. (1994), *Neuron*, 13, 1177–1185 (1994).

The following table sets forth selected Formula I compounds and binding data which demonstrates their usefulness.

| Binding Data of Selected Compounds of Formula I | | |
|---|---|---|
| Compound | Example | Binding Affinity* |
| N-[2-(2,7-dimethoxyfluoren-9-yl)ethyl] propanamide | 5 | +++ |
| N-[2-(2-methoxyfluoren-9-yl)ethyl] butanamide | 6 | ++ |
| N-[2-(2,7-dimethoxyfluoren-9-yl)ethyl] methoxyacetamide | 9 | ++ |
| N-[2-(2-methoxyfluoren-9-yl)ethyl]-2-propenamide | 11 | ++ |
| N-[2-(2,7-dimethoxyfluoren-9-yl)ethyl] cyclobutane carboxamide | 13 | +++ |
| N-[2-(2,7-dimethoxyfluoren-9-yl)ethyl]-2,2-dimethyl propanamide | 14 | + |
| N-[3-(2,7-dimethoxyfluoren-9-yl)prop-1-yl]acetamide | 20 | ++ |
| N-[2-(2-ethoxy-7-methoxyfluoren-9-yl)-ethyl]propanamide | 29 | ++ |

*+++ = IC$_{50}$ < 10 nM; ++ = IC$_{50}$ < 100 nM; + = IC$_{50}$ < 500 nM

Example 35

Measurement of Functional Activity

Cyclic AMP Accumulation in Intact Cells: Melatonin

CELLS:

The media was removed from cell flask and washed with Hank's salt solution or PBS, as appropriate. The cells were detached from flask. Enough media was added so that the concentration of cells is $4 \times 10^5$/ml when counted with a hemocytometer. Dialyzed or heat inactivated fetal bovine serum (FBS) was used in the media when plating the cells. 1 ml of cell suspension was put into each well, then 2 mls of media. Cells were incubated overnight.

SOLUTIONS:

1. Stock solution: plain media (no serum or additives)+20 mM HEPES.

2. IBMX solution: media/HEPES+1 mM IBMX.

3. Assay solution: 90% stock solution+10% IBMX solution.

Each well gets 3 mls of assay solution for preincubation and 3 mls for the assay. Each test condition is done in triplicate.

4. Drug solutions:
   a) Basal assay solution+DMSO
   b) Forskolin stimulation: 10 µM final concentration.
   c) Forskolin+competitor (melatonin): 10 µM final concentration forskolin plus desired concentration of competitor (melatonin).

REACTION:

All tests were done in triplicate at 37° C. Plates with cells were kept in a shallow 37° C. water bath throughout the reaction. Media was taken from the wells and 3 ml of preincubation media was added. After 10 min, that solution was removed and 3 mls of drug solution was added. After 10 min, the media was removed and reaction stopped with HCl. Samples set for at least an hour at room temperature. 1 ml from each dish was taken and put into a microfuge tube and spun to remove floating cells. After dilution to 1:100 for RIA, a radioimmuno-assay was done.

The following table sets forth selected Formula I compounds and intrinsic activity data which demonstrates their usefulness.

| Functional Data of Selected Compounds of Formula I | | |
|---|---|---|
| Compound Name | Ex. | I.A.* |
| N-[2-(2,7-Dimethoxyfluoren-9-yl)ethyl] propanamide | 5 | 1.14 |
| N-[2-(2,7-Dimethoxyfluoren-9-yl)ethyl] butanamide | 10 | 1.15 |
| N-[2-(2,7-Dimethoxyfluoren-9-yl)ethyl] cylopropane carboxamide | 7 | 1.02 |

*I.A. (Intrinsic Activity) = Emax (experimental compound)/Emax (melatonin)
Emax = maximal effect Reasonable variations, such as those which would occur to one having ordinary skill in the art, can be made herein without departing from the scope of the invention.

We claim:

1. A compound of Formula I or a pharmaceutically acceptable solvate thereof:

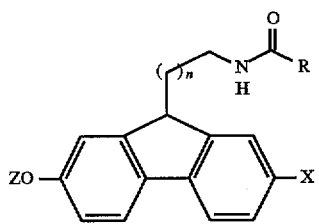

wherein:

X=H, halogen, OH or OZ;

Z=$C_{1-6}$ alkyl; —$(CH_2)_m$—$CF_3$ (m=0-2); $CD_3$ or

n=1 or 2; and

R=$C_{1-6}$ alkyl, $C_{3-6}$ cycloalkyl, $C_{2-4}$ alkenyl, halogen substituted $C_{1-6}$ alkyl, or $C_{1-6}$ alkoxy substituted $C_{1-6}$ alkyl.

2. The compound of claim 1 wherein at least one of X and ZO is methoxy.

3. The compound of claim 2 wherein R is methyl, ethyl, n-propyl, cyclopropyl, cyclopentyl, cyclobutyl or chloromethyl.

4. The compound of claim 3 selected from the group consisting of:
N-[2-(2,7-dimethoxyfluoren-9-yl)ethyl]cyclopentane carboxamide;
N-[2-(2-methoxyfluoren-9-yl) ethyl]butanamide;
N-[2-(2-methoxyfluoren-9-yl)ethyl]acetamide;
N-[2-(2,7-dimethoxyfluoren-9-yl)ethyl]butanamide;
N-[2-(2,7-dimethoxyfluoren-9-yl)ethyl]propanamide;
N-[2-(2,7-dimethoxyfluoren-9-yl)ethyl]cyclopropane carboxamide;
N-[2-(2,7-dimethoxyfluoren-9-yl)ethyl]acetamide;
N-[2-(2-ethoxy-7-methoxyfluoren-9-yl)ethyl]propanamide;
N-[2-(2-hydroxy-7-methoxyfluoren-9-yl)ethyl]propanamide;
N-[2-(2,7-dimethoxyfluoren-9-yl)ethyl]cyclobutane carboxamide; and
N-[2-(2,7-dimethoxyfluoren-9-yl)ethyl]choroacetamide.

5. The compound of claim 2 wherein R is methoxymethyl, methylvinyl, vinyl, isopropyl, or t-butyl.

6. The compound of claim 5 selected from the group consisting of:
5N-[2-(2,7-dimethoxyfluoren-9-yl)-ethyl]but-2-enamide;
N-[2-(2-methoxyfluoren-9-yl)ethyl]-2-propenamide;
N-[2-(2,7-dimethoxyfluoren-9-yl)ethyl]methoxyacetamide;
N-[2-(2,7-dimethoxyfluoren-9-yl)ethyl]-2-methyl propanamide; and
N-[2-(2,7-dimethoxyfluoren-9-yl)ethyl]-2,2-dimethyl propanamide.

7. The compound of claim 2 wherein n=2.

8. The compound of claim 7 selected from the group consisting of:
N-[3-(2,7-dimethoxyfluoren-9-yl)prop-1-yl]propanamide;
N-[3-(2,7-dimethoxyfluoren-9-yl)prop-1-yl]butanamide;
N-[3-(2,7-dimethoxyfluoren-9-yl)prop-1-yl]acetamide;
N-[3-(2,7-dimethoxyfluoren-9-yl)prop-1-yl]cyclobutane carboxamide; and
N-[3-(2,7-dimethoxyfluoren-9-yl)prop-1-yl]cyclopropane carboxamide.

9. The compound of claim 2 wherein X is F, —O(n-pentyl) or

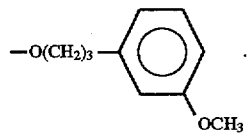

10. The compound of claim 1, N-[2-(2-methoxyfluoren-9-yl)ethyl]butanamide.

11. The compound of claim 1, N-[2-(2,7-dimethoxyfluoren-9-yl)ethyl]propanamide.

12. The compound of claim 1, N-[2-(2,7-dimethoxyfluoren-9-yl)ethyl]cyclobutane carboxamide.

13. The compound of claim 1, N-[2-(2,7-dimethoxyfluoren-9-yl)ethyl]choroacetamide.

14. The compound of claim 1, N-[2-(2,7-dimethoxyfluoren-9-yl)ethyl]butanamide.

15. The compound of claim 1, N-[2-(2,7-dimethoxyfluoren-9-yl)ethyl]acetamide.

16. The compound of claim 1, N-[2-(2,7-dimethoxyfluoren-9-yl)ethyl]cyclopropane carboxamide.

17. The compound of claim 1 wherein X is OZ and Z is $CH_2CF_3$.

18. The compound of claim 1 wherein X is OZ and Z is $CD_3$.

19. A method of treating a sleep disorder in a mammal in need of such treatment comprising administering to said mammal an effective amount of a compound of claim 1.

20. A pharmaceutical composition for treating sleep disorders comprising an effective amount of a compound of claim 1 and a suitable amount of a pharmaceutically acceptable carrier.

* * * * *